(12) United States Patent
Fahraeus et al.

(10) Patent No.: US 6,569,833 B1
(45) Date of Patent: May 27, 2003

(54) CYCLIN DEPENDENT KINASE BINDING PEPTIDES

(75) Inventors: Robin Fahraeus, Dundee (GB); David Philip Lane, Fife (GB)

(73) Assignee: Cyclacel Limited (GB)

( * ) Notice: Subject to any disclaimer, the term of this patent is extended or adjusted under 35 U.S.C. 154(b) by 0 days.

(21) Appl. No.: 09/043,560

(22) PCT Filed: Sep. 23, 1996

(86) PCT No.: PCT/GB96/02340

§ 371 (c)(1),
(2), (4) Date: Apr. 7, 1999

(87) PCT Pub. No.: WO97/11174

PCT Pub. Date: Mar. 27, 1997

(30) Foreign Application Priority Data

Sep. 21, 1995 (GB) ............................................. 9519275

(51) Int. Cl.[7] ........................ A61K 38/00; A61K 38/04; C07K 16/00; C07K 17/00; C07K 5/00
(52) U.S. Cl. ............................ 514/13; 514/14; 514/15; 514/16; 530/326; 530/327; 530/328
(58) Field of Search ................................. 530/326, 327, 530/328; 514/13, 14, 15, 16

(56) References Cited

U.S. PATENT DOCUMENTS

| 5,624,819 A | 4/1997 | Skolnick et al. ............ 435/69.1 |
| 5,739,027 A | 4/1998 | Kamb ..................... 435/240.2 |

FOREIGN PATENT DOCUMENTS

| EP | 0 475 623 B1 | 8/1991 |
| EP | 0 475 623 A1 | 8/1991 |
| EP | 0 518 650 B1 | 6/1992 |
| EP | 0 518 650 A2 | 6/1992 |
| FR | 2 662 698 | 12/1991 |
| WO | WO 91/18981 | 12/1991 |
| WO | WO 92/00757 | 1/1992 |
| WO | WO 94/02167 | 2/1994 |
| WO | WO 94/09135 | 4/1994 |
| WO | WO 95/16771 | 6/1995 |
| WO | WO 95/28483 | 10/1995 |
| WO | WO 95/35115 | 12/1995 |
| WO | WO 97/03635 | 2/1997 |
| WO | WO 97/11174 | 3/1997 |

OTHER PUBLICATIONS

Hannon et al. (1994) Nature 371:257–261.*
Kamb et al. (1994) Science 264: 436–440.*
Okamoto, Aikou et al. "Mutations and Altered Expression of p16$^{INK4}$ In Human Cancer" Proc. Natl. Acad. Sci. USA, vol. 91, pp. 11045–11049 (1994).
Quelle, Dawn E. et al. "Cloning and Characterization of Murine p16$^{INK4a}$ and p15$^{INK4b}$ Genes" Oncogene vol. 11 No. 4 pp. 535–645 (1995).
Serrano, Manuel et al. "A New Regulatory Motif In Cell–Cycle Control Causing Specific Inhibition of Cyclin D/CDK4" Nature vol. 366 pp. 704–706 (1993).
Fahraeus, Robin et al. "Inhibition of pRb Phosphorylation and Cell–Cycle Progression By A 20–Residue Peptide Derived From p16$^{CDKN2/INK4A}$," Current Biology vol. 6, No. 1 pp. 84–91 (1996).
Hannon, Gregory et al. "p15$^{INK4B}$ Is A Potential Effector of TGF–β–Induced Cell Cycle Arrest" Nature vol. 371. pp. 257–261 (1994).
Kamb, Alexander et al. "A Cell Cycle Regulator Potentially Involved In Genesis of Many Tumor Types" Science, vol. 264, pp. 436–440 (1994).

\* cited by examiner

Primary Examiner—Joseph K. McKane
Assistant Examiner—Tomas Friend
(74) Attorney, Agent, or Firm—Lahive & Cockfield LLP; Giulio A. DeConti, Jr.; Cynthia L. Kanik

(57) ABSTRACT

The present disclosure identifies substances having the property of binding to cyclin dependent kinase (cdk) comprising: (i) a peptide including amino acid residue 84 to 103 of full length p16 protein, or an active portion or derivative thereof; or (ii) a functional mimetic of the fragment, active portion or derivative; the substance excludes full length p16, p15, p18 and p19 proteins. These substances are useful in tumor suppression by inhibiting the phosphorylation of Rb protein. Also described herein is the resolution of the amino acid motifs responsible for binding cdks, an FLD motif, corresponding to amino acid residues 90 to 92 of full length p16 protein, and an LVVL motif, corresponding to amino acid residues 94 to 97 of full length p16 protein. The substances disclosed herein can be used in the treatment of hyperproliferative disorders and to screen and design molecules having the similar properties.

22 Claims, 13 Drawing Sheets

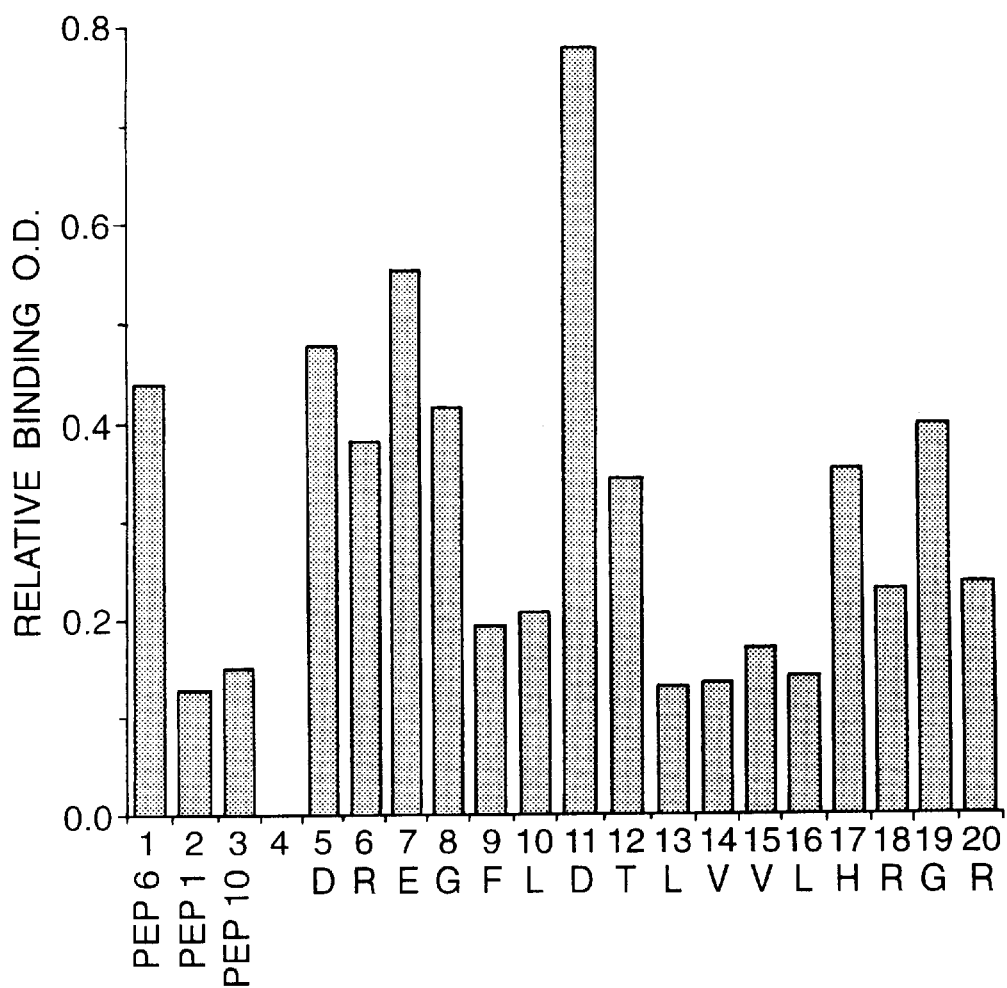

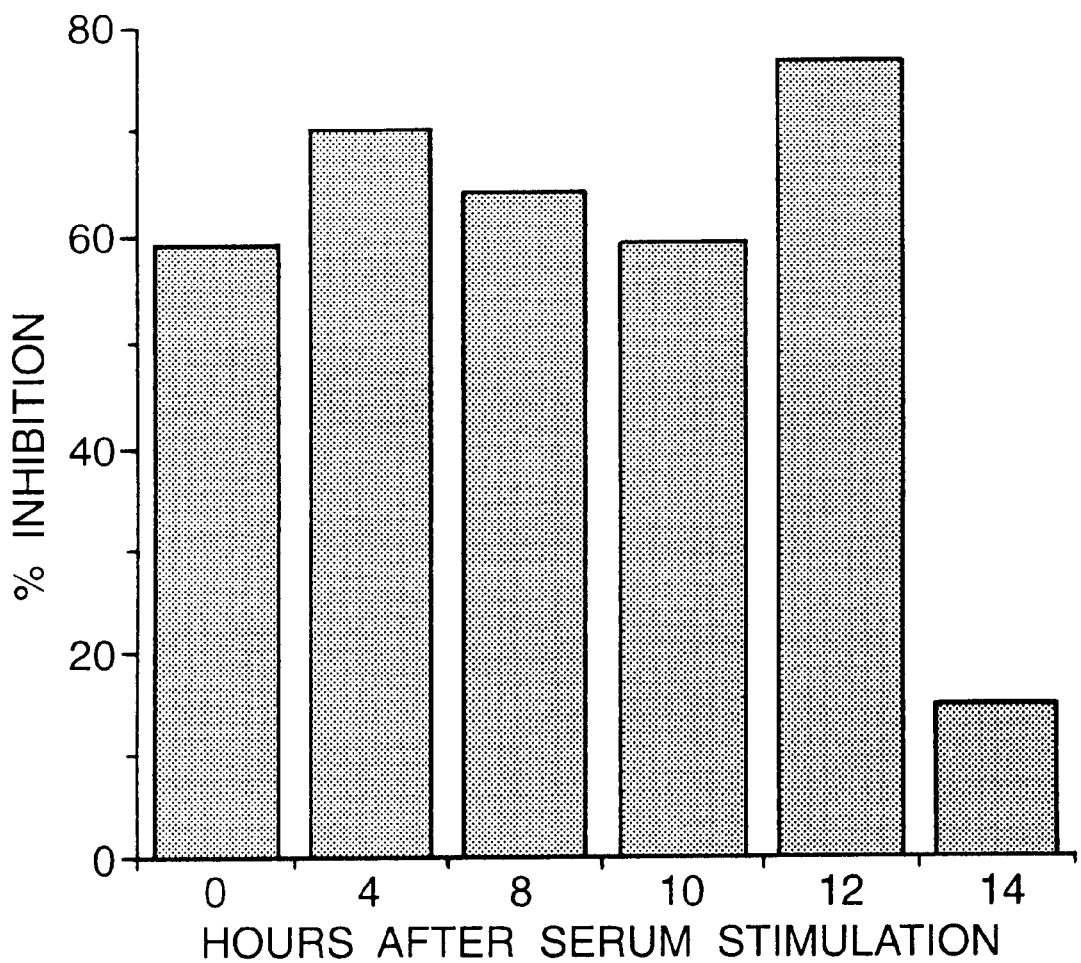

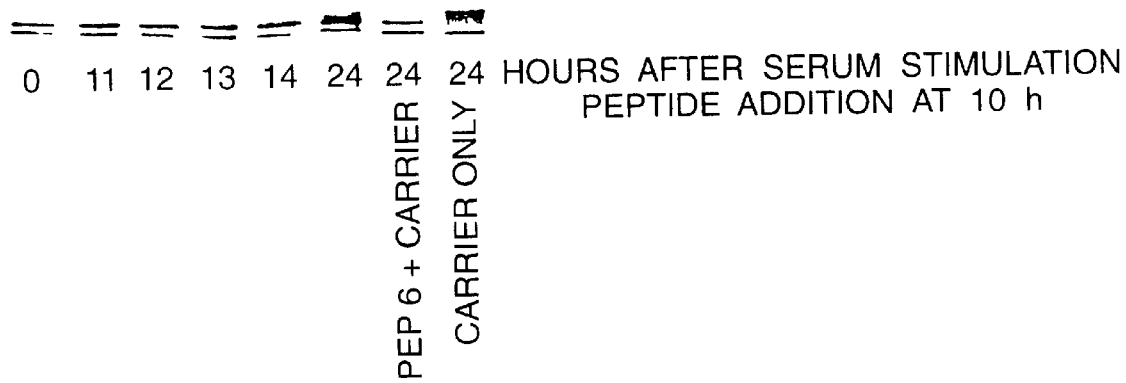

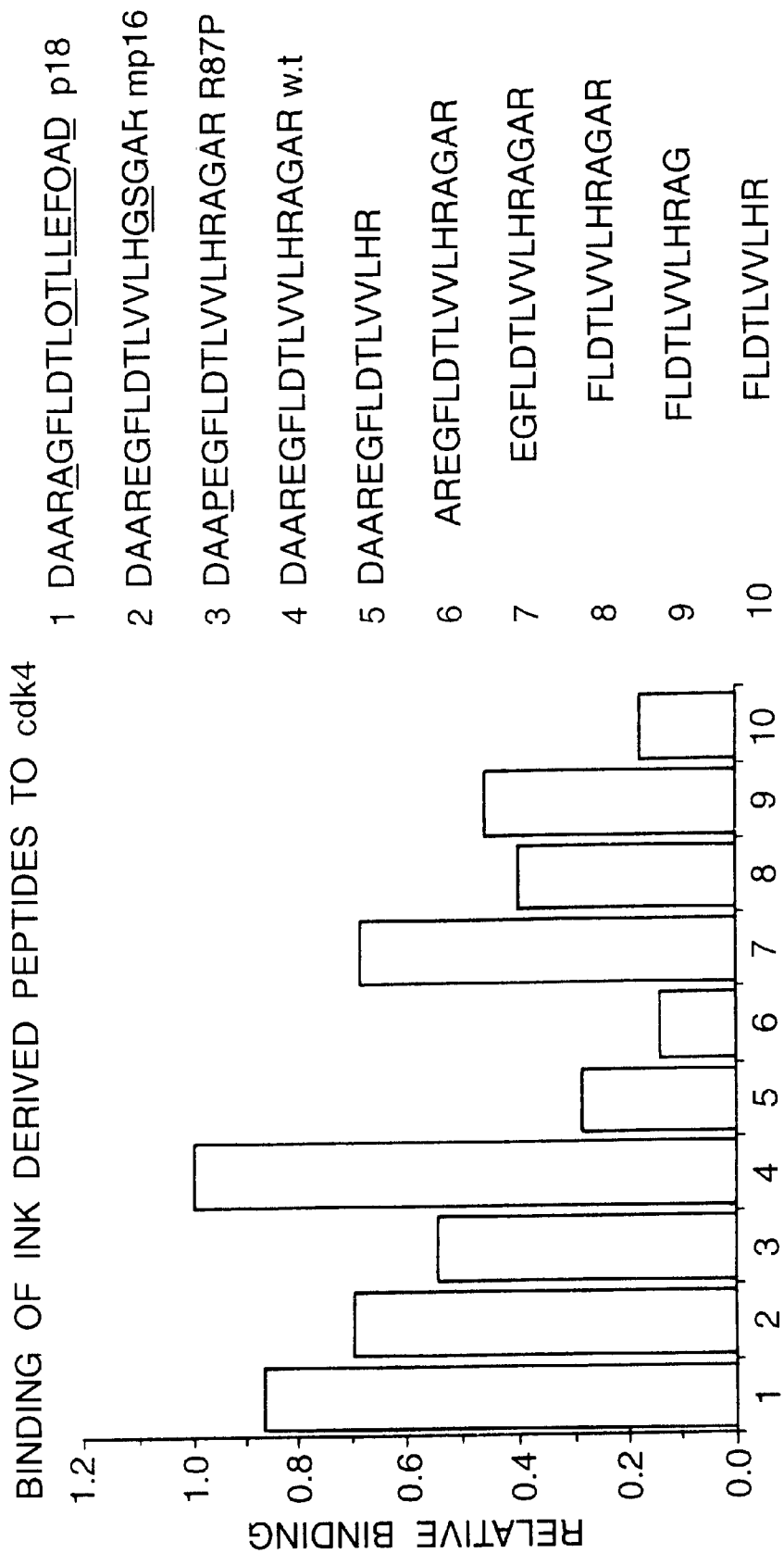

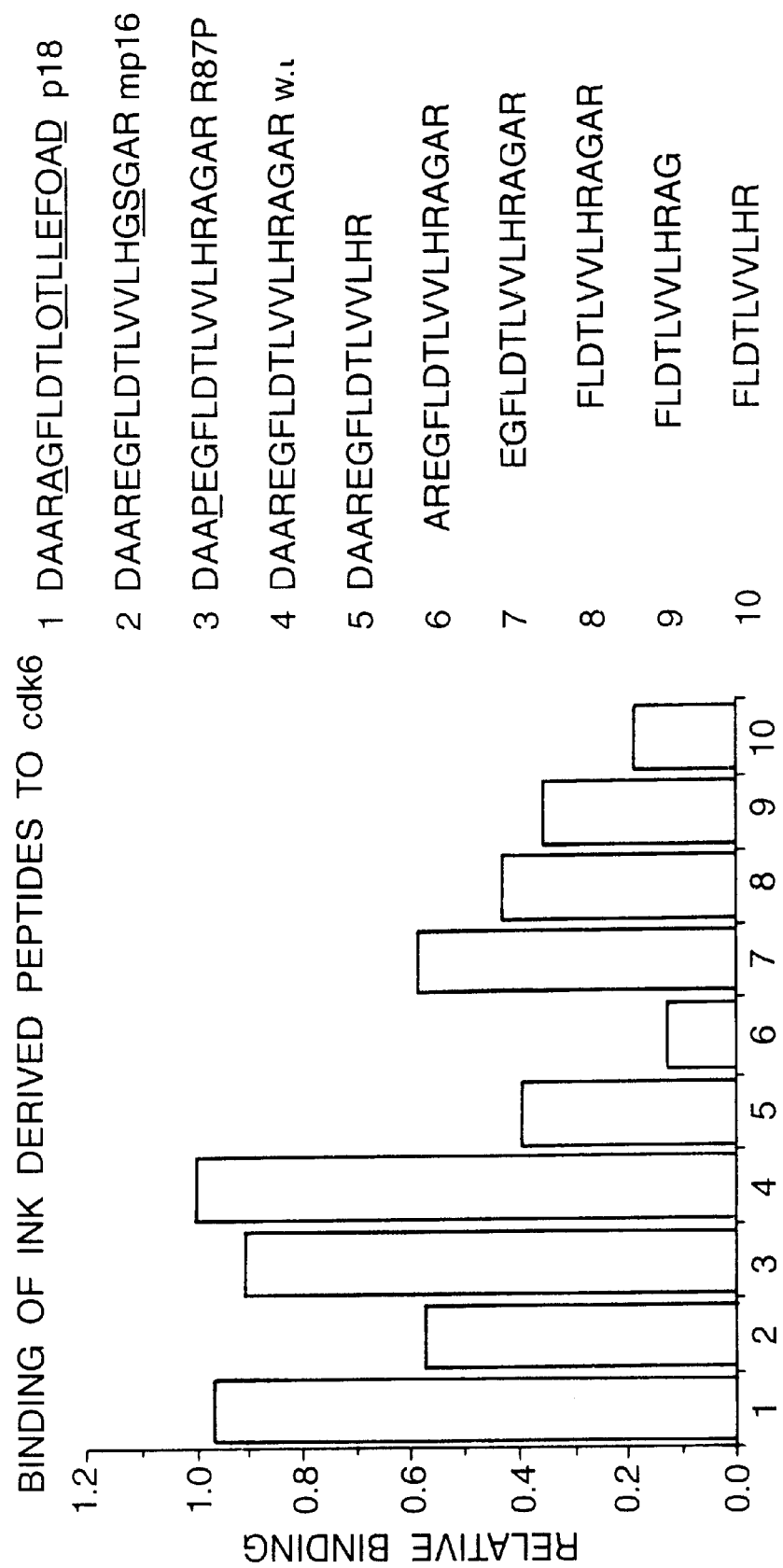

SEQUENCE LISTING

```
<160> NUMBER OF SEQ ID NOS: 16

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Asp Ala Ala Arg Glu Gly Phe Leu Asp Thr Leu Val Val Leu His Arg
1               5                   10                  15

Ala Gly Ala Arg
            20

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Leu Val Val Leu
1

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Ser Gly Ser Gly
1

<210> SEQ ID NO 5
<211> LENGTH: 4
<212> TYPE: PRT
<213> ORGANISM: Artificial Sequence
<220> FEATURE:
```

<223> OTHER INFORMATION: Description of Artificial Sequence: synthetic
      peptide

<400> SEQUENCE: 5

Gly Phe Leu Asp
  1

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: synthetic
      peptide
<223> OTHER INFORMATION: Xaa at position 4 may be any amino acid

<400> SEQUENCE: 6

Phe Leu Asp Xaa Leu Val Val Leu
  1               5

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Asp Ala Ala Arg Ala Gly Phe Leu Asp Thr Leu Gln Thr Leu Leu Glu
  1               5                  10                  15

Phe Gln Ala Asp
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Asp Ala Ala Arg Glu Gly Phe Leu Asp Thr Leu Val Val Leu His Gly
  1               5                  10                  15

Ser Gly Ala Arg
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Asp Ala Ala Pro Glu Gly Phe Leu Asp Thr Leu Val Val Leu His Arg
  1               5                  10                  15

Ala Gly Ala Arg
            20

<210> SEQ ID NO 10
<211> LENGTH: 20
<212> TYPE: PRT
<213> ORGANISM: Artificial Sequence

```
<220> FEATURE:
<223> OTHER INFORMATION: Description of Artificial Sequence: synthetic
      peptide

<400> SEQUENCE: 10

Asp Ala Ala Arg Glu Gly Phe Leu Asp Thr Leu Val Val Leu His Arg
 1               5                  10                  15
Ala Gly Ala Arg
            20

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Asp Ala Ala Arg Glu Gly Phe Leu Asp Thr Leu Val Val Leu His Arg
 1               5                  10                  15

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Ala Arg Glu Gly Phe Leu Asp Thr Leu Val Val Leu His Arg Ala Gly
 1               5                  10                  15
Ala Arg

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Glu Gly Phe Leu Asp Thr Leu Val Val Leu His Arg Ala Gly Ala Arg
 1               5                  10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Phe Leu Asp Thr Leu Val Val Leu His Arg Ala Gly Ala Arg
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: synthetic
      peptide
```

```
-continued

<400> SEQUENCE: 15

Phe Leu Asp Thr Leu Val Val Leu His Arg Ala Gly
 1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Phe Leu Asp Thr Leu Val Val Leu His Arg
 1               5                   10
```

CYCLIN DEPENDENT KINASE BINDING PEPTIDES

This application claims benefit of PCT/GB96/02340, filed Sep. 23, 1996 and United Kingdom patent application 9519245.3, filed Sep. 21, 1995.

FIELD OF THE INVENTION

The present invention relates to substances having the property of binding to cyclin dependent kinase (cdk), and in particular to substances having this property derived from analysis of fragments of p16 protein. The present invention also relates to pharmaceutical compositions comprising these substances and their use in methods of medical treatment, especially in the treatment of hyperproliferative disorders. The invention also relates to methods and uses of these substances in identifying compounds having related activities.

BACKGROUND TO THE INVENTION

Phosphorylation of the Rb gene product (pRb) by members of the cyclin dependent kinase (cdk) family is an important step in the cells commitment to undergo mitosis. This step is regulated in the later part of the G1 phase of the cell cycle at what is known as the restriction (R) point (6). The cdks are key regulatory factors through which both positively and negatively acting cell signal transduction factors merge. Mitogenic stimulation induces an active complex between the D-cyclin, and cdk4 or cdk6 that is capable of phosphorylating pRb in late G1. These kinases are also the targets for cell growth inhibitory signals arising from contact inhibition, growth factor starvation or TGF-β. The inhibitory signals can block kinase activity by inducing the production or activity of different members of the two rapidly enlarging families of INK4 and p21/KIP cdk-inhibitors that either interfere directly with the kinases or with the cyclin-kinase complexes (7). The family of INK proteins that have been identified consists of p15, p16, p18 and p19 (20, 22, 23).

However, unlike p21$^{cip1/WAF1}$, which is indirectly linked to tumour suppression activity through p53 transcriptional stimulation (8), the INK4p16 gene is itself deleted or mutated in a large number of human tumours (9–15). Germ line mutations in INK4p16 have been associated with an increased risk of developing melanoma (9,10). The 156 amino acid product of the INK4p16 gene is known as CDKN2 or p16INK4a (referred to in this application as "p16").

SUMMARY OF THE INVENTION

We set out to identify and study the region of p16 that interacts with cyclin dependent kinases such as cdk4 and cdk6, and to investigate applications of these properties, in particular the possibility that the binding of cdks by substances comprising a peptide based on this region of p16 could be used in tumour suppression by inhibiting the phosphorylation of Rb protein.

Small peptides can sometimes be powerful tools to identify regions of proteins involved in protein-protein interactions and biological activity (16–19). In this work, we synthesised a series of overlapping 20 amino acid (aa) peptides that spanned the p16 amino acid sequence, and tested the capacity of each biotinylated peptide to interact with $^{35}$S-labelled cdk4 and cdk6 expressed in rabbit reticulocyte lysates.

These experiments identified a 20 amino acid synthetic peptide corresponding to residues 84 to 103 of p16 that interacts with cdk4 and cdk6, and inhibits cdk4-cyclin D1 mediated phosphorlotion of Rb protein in vitro. An alanine substitution series defined amino acid residues important for the cdk4 and cdk6 interaction and for the inhibition of Rb phosphorylation. In this application, residues 84 to 103 of p16 correspond to the sequence sets out in FIG. 1C, i.e. DAAREGFLDTLVVLHRAGAR (SEQ ID NO:1).

Further, when coupled to a small peptide carrier molecule and applied directly to tissue culture medium, the p16-derived peptide blocked cell cycle entrance into S-phase in both serum starved human HaCaT cells and other types of cells that are cycling normally. This was associated with an inhibition of pRb phosphorylation in vivo. These results demonstrate that a p16-derived synthetic peptide coupled to a small carrier molecule can mimic the G1-phase arrest associated with overexpression of full length p16 protein. This provides a route to the restoration of the p16 suppressor gene function in human tumours.

Accordingly, in a first aspect, the present invention provides a substance having the property of binding to cyclin dependent kinase (cdk) comprising:
  (i) a peptide including amino acid residues 84 to 103 of full length p16 protein, or an active portion or derivative thereof; or,
  (ii) a functional mimetic of the fragment, active portion or derivative;
  wherein the substance excludes full length p16, p15, p18 and p19 proteins;

Preferably, the cyclin dependent kinase (cdk) is cdk4 or cdk6. The substance preferably also has the property of inhibiting the phosphorylation of Rb protein which is mediated by a complex formed between cdks and cyclin D. This in turn can be used to block cellular differentiation by preventing the entry of cells into the S-phase. As the substances bind cyclin dependent kinases, they can also be used to prevent the formation of the complex between cdks and cyclin D, having the additional biological effect of increasing cyclin D levels in cells. As well as blocking cdk4 and cdk6 dependent phosphorylation of pRb, the substances described herein could be used to target other cellular substrates, including the pRb family members p107 and p130, or other substances that are targets for cdk4 and cdk6 mediated regulation.

In the present invention, "an active portion" means a portion of the peptide which is less than the full amino acid sequence of the fragment above, but which retains the property of binding to a cyclin dependent kinase (cdk). Preferably, the peptide also has the property of inhibiting pRb phosphorylation.

In the present invention, a "derivative" is a protein modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the proteins. As an example, a derivative of peptide 6 in which aspartic acid 92 was substituted for alanine was found to be more potent than the peptide 6 (residues 84 to 103) in binding to cdk4 and cdk6, and having a greater inhibition of pRb phosphorylation. Other derivatives include inserting one or more amino acid residues between amino acid motifs FLD ard LVVL.

In the present invention, "functional mimetic" means a substance which may not contain a fragment or active portion of the p16 amino acid sequence, and probably is now a peptide at all, but which has some or all of the properties of the p16 fragment, in particular the property of binding to a cyclin dependent kinase and/or inhibiting pRb phosphorylation.

In a preferred embodiment, the peptide includes residues 89 to 97 of full length p16 protein. More preferably, the peptide includes the peptide motif FLD, corresponding to amino acids 90 to 92 of full length p16 protein, and/or the peptide motif LVVL (SEQ ID NO:2), corresponding to amino acids 94 to 97 of full length p16 protein. We have also found that both the D and L isoforms of the peptides share the property of binding to cdk and/or inhibiting pRb phosphorylation.

In a further aspect, the present invention provides compounds comprising any of the above substances coupled to carrier molecules, enabling the compounds to be delivered to cells in vivo. In one embodiment, the carrier molecule is a 16 aa peptide sequence derived from the homeodomain of Antennapedia (e.g. as sold under the name "Penetratin"), which can be coupled to one of the above substances via a terminal Cys residue. The "Penetratin" molecule and its properties are described in WO 91/18981.

In a further aspect, a substance comprising one of the above peptides can be stabilised by coupling to another peptide sequence. Preferably, this allows the peptide to adopt a conformation more closely resembling that of full length p16, typically having the advantage of increasing the activity of the peptide relative to the uncoupled fragment, e.g. so that the peptide fragment has an activity more closely approaching or surpassing that of full length p16.

In further aspects, the present invention provides pharmaceutical compositions comprising one or more of the above substances and the use of these compositions in methods of medical treatment. In a preferred embodiment, the present invention relates to the use of these substances in the preparation of medicaments for the treatment of hyperproliferative disorders, such as cancer, psoriasis or arteriogenesis. In particular, cancers which are p16 negative or associated with the overexpression of cdks are especially likely to respond well to compositions comprising one or more of the above substances.

Pharmaceutical compositions according to the present invention, and for use in accordance with the present invention, may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes. For such administration, a parenterally acceptable aqueous solution may be employed which is pyrogen-free and has suitable pH, isotonicity and stability. Those skilled in the art are well able to prepare suitable solutions. Preservatives, stabilisers, buffers, antioxidants and/or other additives may be included, as required. Dosage levels can be determined by the those skilled in the art, taking into account the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed). 1980.

In embodiments in which the substances are proteins, the present invention also provides nucleic acid encoding these proteins. Those skilled in the art can readily construct such nucleic acid sequences from the amino acid sequences disclosed herein, taking account of factors such as codon preference in the host used to express the nucleic acid sequences. In embodiments of the invention in which he protein is coupled to a carrier protein, nucleic acid encoding the carrier protein can be linked to the sequence encoding the peptides and the sequences expressed as a fusion.

In further aspects, the present invention provides vectors incorporating the above nucleic acid and host cells transformed with the vectors.

In a further aspect, the present invention provides the use of any one of the above substances in screening for (i) compounds having one or more of the biological activities of the substances described above or (ii) compounds which are binding partners of one of the substances, e.g. antibodies or complementary peptides specific for p16 or a p16 mimetic. Preferably, the substances are peptide fragments of p16 protein. Examples of screening procedures for mimetics or binding partners include:

(a) immobilising the p16 fragments on a solid support and exposing the support to a library of labelled peptides or other candidate compounds, and detecting the binding of the peptides or candidate compound to the p16 fragments;

(b) using labelled cdks and a library of unlabelled candidate compound or peptides;

(c) other combinations of solid phases substrates and binding measurements;

(d) Western blots using the fragments of pig protein and antibodies raised to the p16 fragments and determining the displacement of the antibodies by candidate compounds;

(e) using yeast two hybrid screens to detect candidate peptides which bind to the p16 peptide or to oligonucleotides derived from the p16 fragments (for a description of yeast two hybrid screens see our earlier application WO 96/14334);

(f) using the fragments of p16 protein and/or candidate compounds in cell systems to determine whether the fragments or candidate compounds inhibit phosphorylation of Rb and/or prevent the cells from cycling;

(g) using the fragments of p16 protein and/or candidate compounds in animal models of tumour growth to determine whether the fragments or candidate compounds prevent the occurrence of tumours, reduce tumour size, inhibit tumour growth and/or inhibit tumour cell migration.

In a further aspect, the present invention provides method of identifying compounds which compete with one of the above substances, the method comprising:

(a) binding a predetermined quantity of the substance which is detectably labelled to a cyclin dependent kinase (cdk);

(b) adding a candidate compound; and, (c) determining the amount of the labelled compound that remains bound to the cdk or which becomes displaced by the candidate compound In a further aspect, the present invention provides a method of identifying mimetics of one of the above substances, the method comprising:

(a) immobilising one or more candidate compounds on a solid substrate;

(b) exposing the substrate to a labelled cyclin dependent kinase (cdk);

(c) selecting the candidate compounds that bind to cdk.

In the above aspects, preferably the cyclin dependent kinase is cdk4 or cdk6. Preferably, the substance is a fragment of p16 protein, and more preferably the FLD and LVVL motifs disclosed above. Conveniently, the candidate compounds can be selected from a synthetic combinatorial library.

The present invention may further comprise testing the candidate compound for the property of inhibiting pRb phosphorylation and/or testing the compound for the property of inhibiting the entry of cells into the S-phase.

In a further aspect, the present invention provides the use of a fragment of p16 protein including the amino acid motifs FLD, corresponding to amino acid residues 90 to 92 of full length p16 protein, and/or LVVL, corresponding to amino acid residues 94 to 97 of full length p16 protein in the design of an organic compound which is modelled to resemble the three dimensional structure of said amino acid motifs, the organic compound having the properties of binding to cyclin dependent kinase and/or inhibiting pRb phosphorylation.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

By way of example, the present invention will now be described in more detail with reference to the accompanying figures. The following examples are provided to illustrate the present invention, and should not be interpreted as limiting the scope of the claims.

BRIEF DESCRIPTION OF THE DRAWINGS

FIGS. 1A and 3 show the relative binding of the p16 derived peptides to in vitro expressed cdk4 or cdk6.

FIG. 1C shows peptide 6 corresponds to amino acids 84 to 103 of the p16 protein.

FIGS. 1D and E show similar binding to in vitro translated cdk4 and cdk6 of an alanine substitution series of peptide 6 amino acids. The amino acid residues substituted by alanine are indicated and the relative amount of cdk4 and cdk6 precipitated by each peptide is shown. Substituting the hydrophobic residues corresponding to amino acids 89–90 and 94–97 to alanine decreases the binding of peptide 6 to both kinases, while substitution of Asp92 significantly increases the interaction.

FIG. 3 shows the inhibition of S-phase entry of human keratinocyte derived HaCaT cells with peptide 6 coupled to a small peptide carrier. Cells were synchronised in G0 by serum starvation for 72 hours before serum and 10 $\mu$M BrdU were added. FIG. 3A shows the indicated time points after serum stimulation when 100 nM peptide 6 coupled to the Penetratin carrier molecule was added to the tissue culture medium. The data presented show % inhibition of cells entering S-phase after incubation with peptide 6 coupled to Penetratin in relation to cells incubated with serum only.

FIG. 4B shows the status of pRb phosphorylation in HaCaT whole cell extracts as determined by Western blot analysis. Cells were starved for 72 hours before serum was added and harvested at the indicated time points. Peptide 6 coupled to Penetratin or Penetratin by itself was added at 10 hours as indicated.

FIGS. 5B and 5C show the corresponding determination of the binding of the INK family members and fragments to cdk4 and cdk6. The sequence DAARAGFLDTLQTLLEFQAD corresponds to SEQ ID NO:7, the sequence DAAREGFLDTLVVLHGS-GAR corresponds to SEQ ID NO:8, the sequence DAAPEGFLDTLVVLHRAGAR corresponds to SEQ ID NO:9, the sequence DAAREGFLDTLVVLHRAGAR corresponds to SEQ ID NO:10, the sequence DAAREG-FLDTLVVLHR corresponds to SEQ ID NO:1, the sequence AREGFLDTLVVLHRAGAR corresponds to SEQ ID NO:12, the sequence EGFLDTLVVLHRAGAR corresponds to SEQ ID NO:13, the sequence FLDTLVVL-HRAGAR corresponds to SEQ ID NO:14, the sequence FLDTLVVLHRAG corresponds to SEQ ID NO:15, and the sequence FLDTLVVLHR corresponds to SEQ ID NO:16.

DETAILED DESCRIPTION

Materials and Methods

Peptide Precipitation

A 20 aa peptide library with a 5 aa overlap of p16 (apart from the first 8 N-terminal residues) was synthesised adding a SGSG linker to the N-terminus to which a biotin group was coupled. The alanine substitution series of peptide 6 was synthesised in the same way. The peptides were coupled to streptavidin immobilised on agarose beads and washed 4 times in PBS before incubating for 1 hour on ice with rabbit reticulocyte lysate (Promega) containing $^{35}$S-methionine labelled cdk4 or cdk6. The beads were washes 4 times in 1.2×PBS with 0.2% Triton X-100 before addition of SDS loading buffer and applied to 12% SDS polyacrylamide gels. The gels were exposed to an autoradiography film and the bands corresponding to cdk4 and cdk6 were analysed by densitometry.

pRb Phosphorylation in vitro

Figure 2A:
FIG. 2A shows the inhibition of phosphorylation of $E.\ coli$ expressed and purified full length Rb protein. p16 derived wild type peptides (peptides 1, 6 and 10) or the peptide 6 alanine substitution series were tested for their capacity to interfere with pRb phosphorylation by lysates from Sf9 insect cells containing cdk4. Peptides 1 and 10 of the p16 series do not precipitate cdk4 or cdk6 and do not affect pRb phosphorylation. Peptide 6 binds to cdk4 and cdk6 and significantly reduces the level of pRb phosphorylation. The amino acid residues of the peptide 6 substituted with alanine are indicated and the levels of pRb phosphorylation in the presence of each peptide are shown. The Ala-Asp substitution at residue 92 (Ala92) inhibits phosphorylation of the full length Rb protein even more efficiently than the wild type peptide 6, reflecting its more potent binding to cdk4 and cdk6. Alanine substitution of the hydrophobic residues at positions 90 and 95–97 or closely adjacent residues reduced the inhibitory capacity to background levels.
Figure 2B:
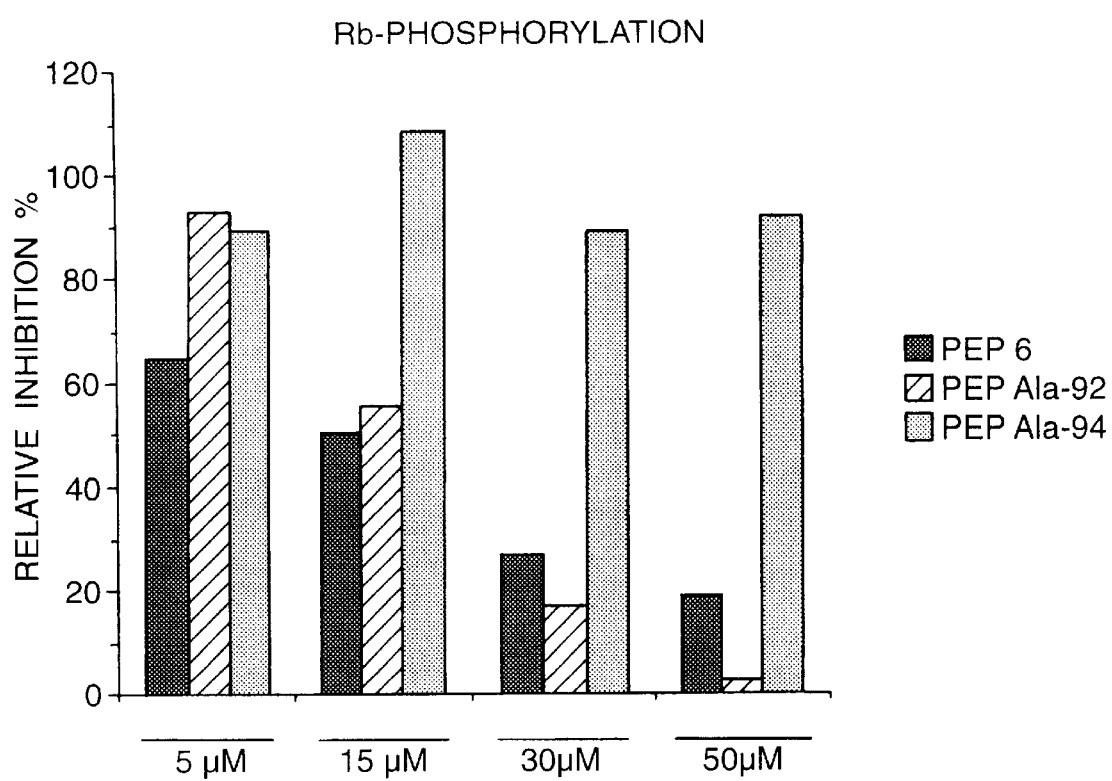
FIG. 2B shows the effect of increasing amounts of peptides 6, Ala92 and Ala94 on pRb phosphorylation. At 50 $\mu$M the block of cdk4-cyclin D dependent pRb phosphorylation by peptide Ala-92 is nearly complete.

Peptides were incubated at a concentration of 25 mM in a buffer containing 50 mM Hepes pH 7.4, 10 mM $MgCl_2$, 2.5 mM EGTA, 1 mM DTT, 10 mM β-glycerophosphate, 1 mM NaF and 1 mM $Na_3VO_4$ and 3 ml of extract from Sf9 insect cells infected with human cdk4-expressing baculovirus lysed in 10 mM Hepes pH 7.4, 10 mM NaCl, 1 mM EDTA and 0.5 mM PMSF. The mixture was incubated for 60 minutes on ice. Human cyclin D containing Sf9 lysate (3 ml) prepared as above was added together with 0.6 mg of purified recombinant full length Rb protein and 2.5 mM $^{32}$P ATP in a final concentration of 50 mM ATP and incubated for 10 minutes at +30° C., the reaction was terminated by addition of SDS loading buffer and loaded onto 8% SDS polyacrylamide gels. The gels were either exposed to autoradiographic film (FIG. 2A) or the levels of pRb phosphorylation were estimated by a Phosphoimager (FIG. 2B).

Cell Cycle Inhibition

Figure 3B:
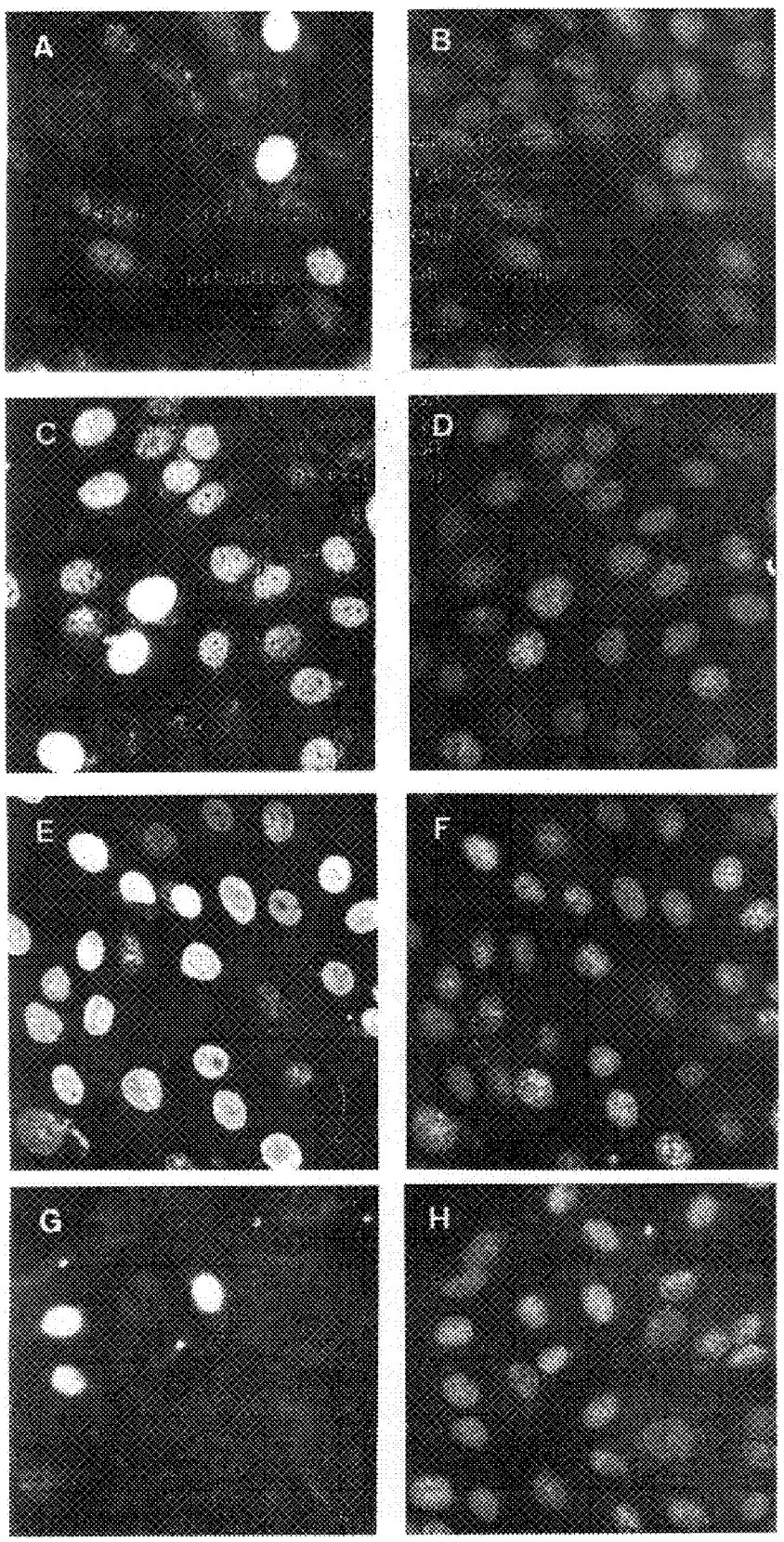
FIG. 3B sets out panels A, C, Z and G which show cells synthesising DNA by BrdU labelling, and panels B, D, F and H show the same fields of cells stained with Hoescht. The percentage of cells that incorporated BrdU after serum stimulation was 71% at 24 hours (E and F) and 14% (G and H) at 3 hours. The number of cells incorporating BrdU at 24 hours was significantly reduced when peptide 6 coupled to the Penetratin carrier molecule was added at 12 hours (panel A and B) compared to at 14 hours (panel c and D) No effect on DNA synthesis could be observed with Penetratin only (not shown).

A cysteine residue was added to the C-terminus of peptide 6 and used for coupling to the 16 amino acids long Penetratin peptide (amino acid sequence RQIKIWFQNRRMKWKK)(SEQ ID NO:3) of the Antennapedia homeodomain (24) (Appligen) by means of a disulzhide bond. Cells were seeded on cover slips prior to starvation for 72 hours in DMEM medium without FCS. The medium was substituted by DMM containing 10% FCS and BrdU. The coupled peptides were added at different time points after serum stimulation. The number of cells entering S-phase was determined by estimating the numbers of cells incorporating BrdU at 24 hours by fixing the cells on cover slips in acetone/methanol (1:1), incubating in 1M HCl for 30 minutes, washing 6 times in PBS and then incubating with anti-BrdU monoclonal antibody and Texas Red conjugated secondary antibody and mounted in Mowiol containing Hoescht. At least six different areas on three different cover slips were counted for each single experiment which was repeated at least two times. The values presented in FIG. 3A show one representative experiment.

FACS Analysis

Twenty minutes before harvest, cells were incubated with 10 μM BrdU. Tryptinised cells were then washed in PBS and resuspended in 1 ml of PBS and carefully mixed with 3 ml of 96% EtOH and incubated for 1 hour at 4° C. The cells were then incubated in 2 ml of 30 mM HCl containing 1 mg/ml of Pepstatin for 30 mins at 37° C. before incubation in 2M HCl for 15 minutes. After careful washing 6 times in PBS, the cells were incubated in 200 μl (1:50) of anti-BrdU antibodies (Becton Dickinson) for 1 hour at room temperature. After washing in PBS, the cells were incubated in FITC conjugated anti-mouse IgG (1:80) (Sigma) for 30 mins.

After washing, the cells were resuspended in is PBS containing 25 μg/ml of Propidium iodine and analysed on FACS.

pRb Phosphorylation in vivo

Hyperphosphorylated pRb was extracted from cells cultured on cover slips by treating the cells with hypotonic buffer containing 0.1% Triton X-100 prior to fixation in acetone/methanol (1:1) (26). Fixed cells were incubated for 1 hour with anti-pRb monoclonal antibody IF8, washed 3 times in PBS and incubated for 45 minutes with Texas Red conjugated secondary antibody before the cover slips were mounted in Mowiol containing Hoescht.

For Western blot analysis, cells were lysed in RIPA buffer containing 50 mM Tris pH8.0, 150 mM NaCl, 1.0% NP-40, 0.5%. DOC, 0.1% SDS and 0.1 mM PMSF for 30 minutes at +4° C. The protein concentrations were determined before the samples were boiled in SDS loading buffer, run on 8% SDS polyacrylamide gels and transferred to a nitrocellulose membrane. The filters were first incubated with anti-pRb monoclonal antibody IF8 before being incubated with a horse radish peroxidase (HRP) conjugated secondary antibody (DAKO) and developed with ECL (Amersham).

Site Directed Mutagenesis

The VV.95,96AA mutations were introduced into wild type his-tagged p16 protein using the transformation site-directed mutagenesis kit from Promega, according to manufacturer's instructions. The mutations were introduced by changing the corresponding codons from GTG GTG to GCG GCG and then confirming the sequence by DNA sequencing.

Results

Identification of a Region of p16 That Binds to cdks

Figure 1A:
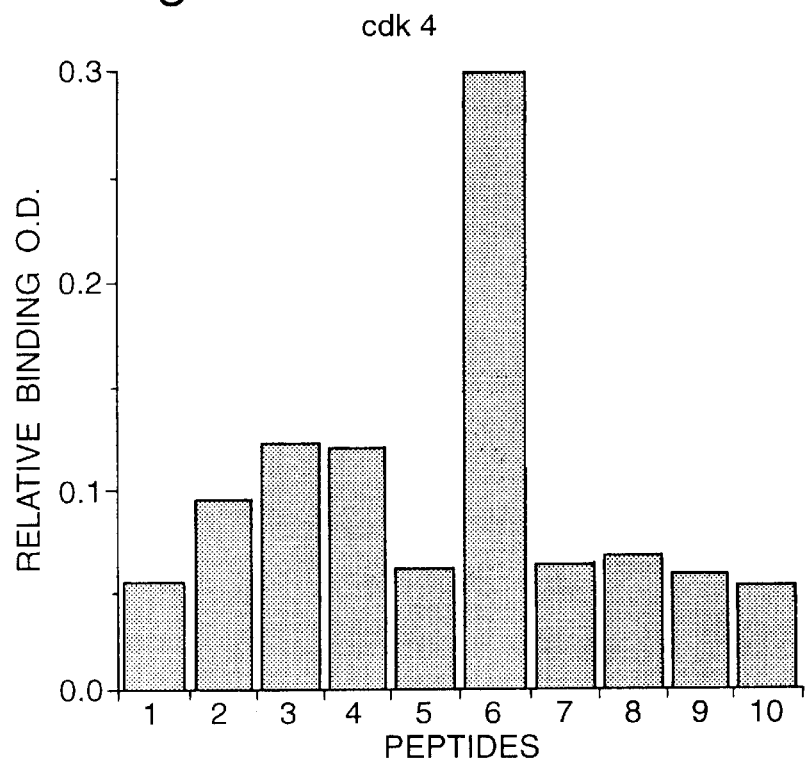
Figure 1B:
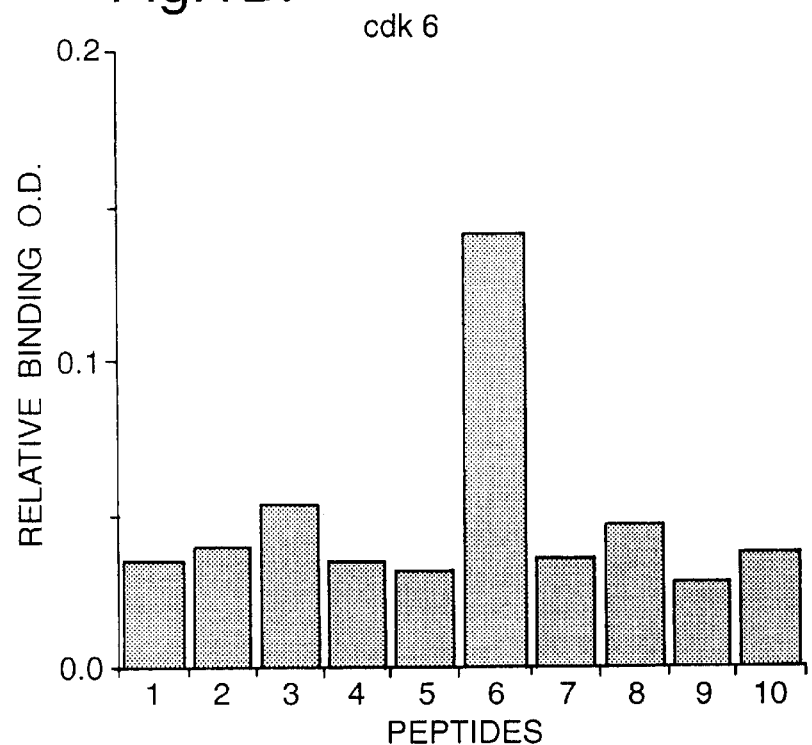
Figure 1E:
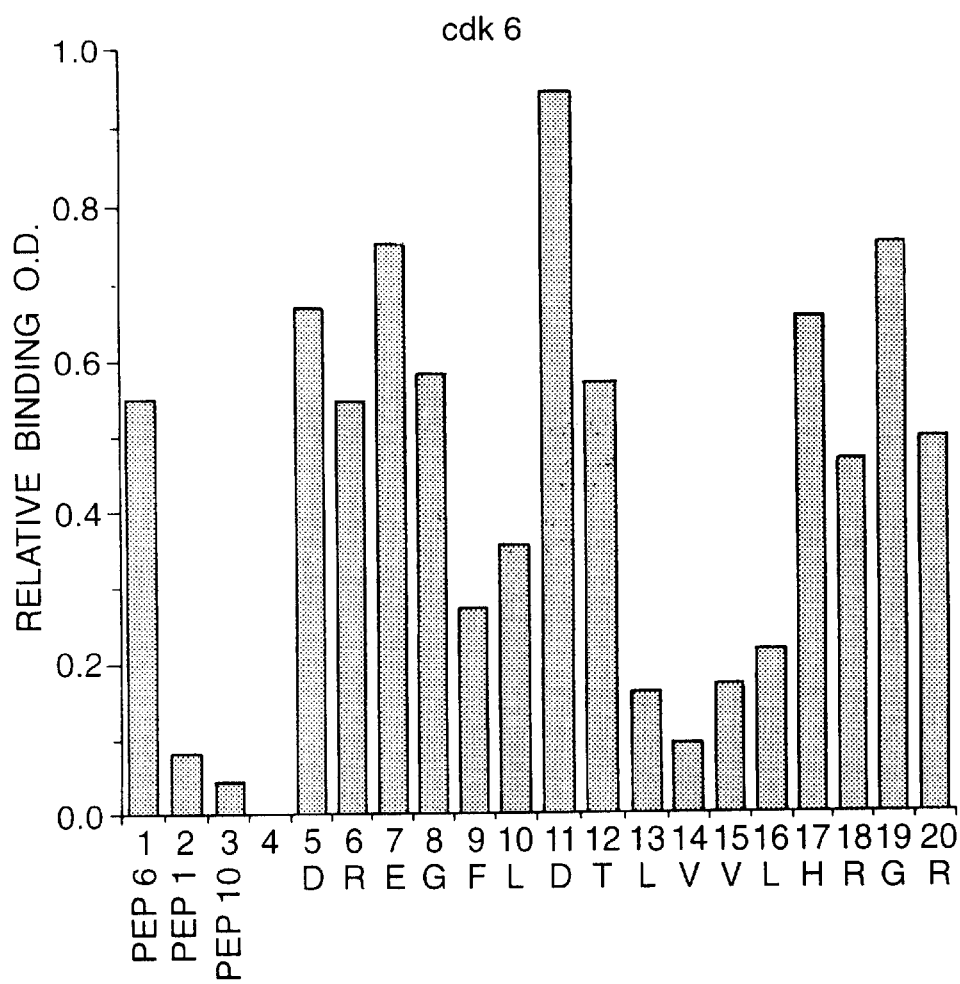
Figure 1F:
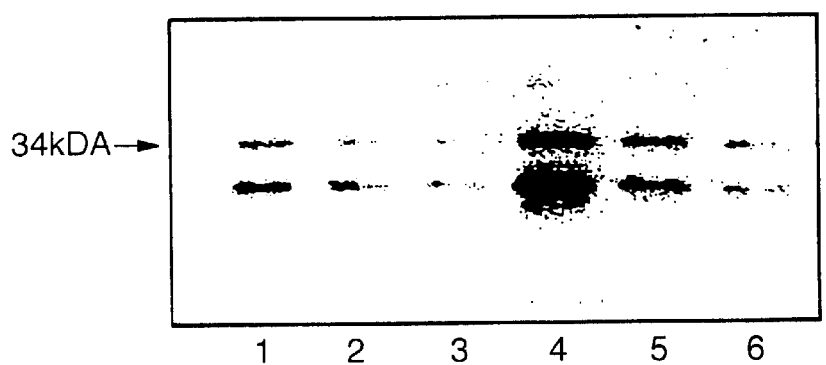
FIG. 1F shows results from an experiment in which Sf9 insect cell lysates containing cdk4 were incubated with the following biotinylated peptides: peptide 6 (lanes 1 and 4), peptide 1 (lanes 2 and 5) and peptide 10 (lanes 3 and 8). The complexes were precipitated with streptavidin-coated agarose beads. The lower of the cdk4 bands is related to the extraction method (see Materials and Methods). These results show that if cyclin D1 containing insect cell lysates were added to cdk4 prior to the addition of peptide, the extracts containing the peptide can not bind the cdk4. However, if the peptides are added to the cdk4 prior to cyclin D1, the peptide binds cdk4, suggesting that the peptides can be sued to interfere in the binding between cyclin D and cdks.

FIGS. 1A and B show that a peptide corresponding to aa 84 to 103 of p16 (peptide 6) when coupled to streptavidin agarose beads can be used to extract both cdk4 and cdk6 from the reticulocyte lysates. An alanine substitution series of this peptide (FIG. 1C) revealed that substitution of hydrophobic amino acids in the region between residues 89 to 96 decreased the capacity of the peptide to bind both cdk4 and cdk6. Interestingly, substitution of aspartic acid 92 with alanine significantly increased the binding of the peptide to both kinases (FIGS. 1D and E).

p16 Fragments and the Inhibition of pRb Phosphorylation

In order to study the functional significance of p16 peptide interactions with the cyclin dependent kinases we asked whether the p16 derived peptides, as well as the alanine-substitution series of peptide 6, affected cdk4-cyclin D ability to phosphorylate pRb in an in vitro assay (FIG. 2). Only peptide 6 of the p16-derived series significantly decreased pRb phosphorylation (only results from peptides 1, 6 and 10 are shown). A correlation was observed between the capacity of the various peptides in the alanine-substitution series to bind cdk4 and cdk6 and the level of inhibition of cdk4-cyclin D1 kinase activity.

The Effect of Mutations in the p16 Binding Domain

Most significantly, substitution of amino acids in, or adjacent to, the two hydrophobic regions located between residues corresponding to aa 89 to 96 of the full length p16 protein resulted in a decrease of the peptide 6 induced inhibition of pRb phosphorylation. Interestingly, the change of aspartic acid 92 to alanine resulted in a peptide more potent than peptide 6 in inhibition of the cdk4 kinase activity. A dilution series revealed that at 50 μM peptide concentration, pRb phosphorylation was almost completely blocked by the Ala92 peptide and peptide 6. In contrast, the single substitution Ala94 completely inactivates the function of peptide 6 in this assay (FIG. 2B). The correlation between the enhanced binding of the Ala92 peptide and its greater efficiency as a kinase inhibitor is provocative and suggests that further variants of the peptide 6 sequence might possess greater activity, perhaps by encouraging the peptide to adopt a conformation more similar to that of the active inhibitory site on the native p16 protein. A comparison of the work described here in identifying the inhibitory region of p16 represented by peptide 6 and other related proteins shows that an identical motif is present in the corresponding domain of the kinase inhibitor p15 (20,21) and is conserved in the closely related p18 (21) and p19 (22,23) inhibitors, although prior to this work this similarity and its significance was not realised by those skilled in the art.

Point mutations in the p16 gene have been found in tumours from familial and primary melanomas as well as in tumours from the oesophagus and the bladder (9,10, 14, 15). Some of these mutants are clustered in, or near, the region encompassed by peptide 6, and have been shown to have lost their ability to inhibit cell proliferation and pRb phosphorylation(3,4,12). This further supports the importance of this region for p16 protein function.

Mutations in the p16 protein that result in its inactivation and are outside of the region suggested above that mediates the binding to cdk have been shown to induce global conformation changes of the p16 protein or are temperature sensitive, suggesting that these mutations might affect the structure of the domain we suggest mediates binding. Furthermore, deletion of the p16 N- or C-terminus both result in p16 inactivation, supporting the deduction that the structure of p16 is sensitive.

Effect of p16 on Cell Proliferation and the Use of Carrier Peptides

Since overexpression of p16 in cultured cells can block S-phase entry (1–4), we wanted to see if peptide 6 could affect cell proliferation. A 16aa region of the Antennapedia homeodomain that has been shown to translocate through biological membranes in a rapid and energy independent fashion (24) was coupled as carrier to peptide 6 and added to the tissue culture medium of serum-starved human keratinocyte derived HaCaT cells.

FIG. 3 shows that when 0.1 μM of the p16 peptide coupled to the carrier molecule was added at the same time or up to 12 hours after the addition of serum, the number of cells entering S-phase were reduced dramatically according to BrdU incorporation measured at 24 hours after serum addition. However, when the coupled peptide was added to the medium 14 hours after addition of serum, the number of cells entering S-phase was the same as that seen in cells not treated with peptide. This suggests that the effect of the peptide is limited to a rather narrow window in the cell cycle that corresponds to the later part of G1. This includes the restriction (R) point at which serum stimulation and protein synthesis are no longer required to ensure entry into S-phase and which has been suggested to be the critical time of pRb phosphorylation (6,25).

Figure 4A:
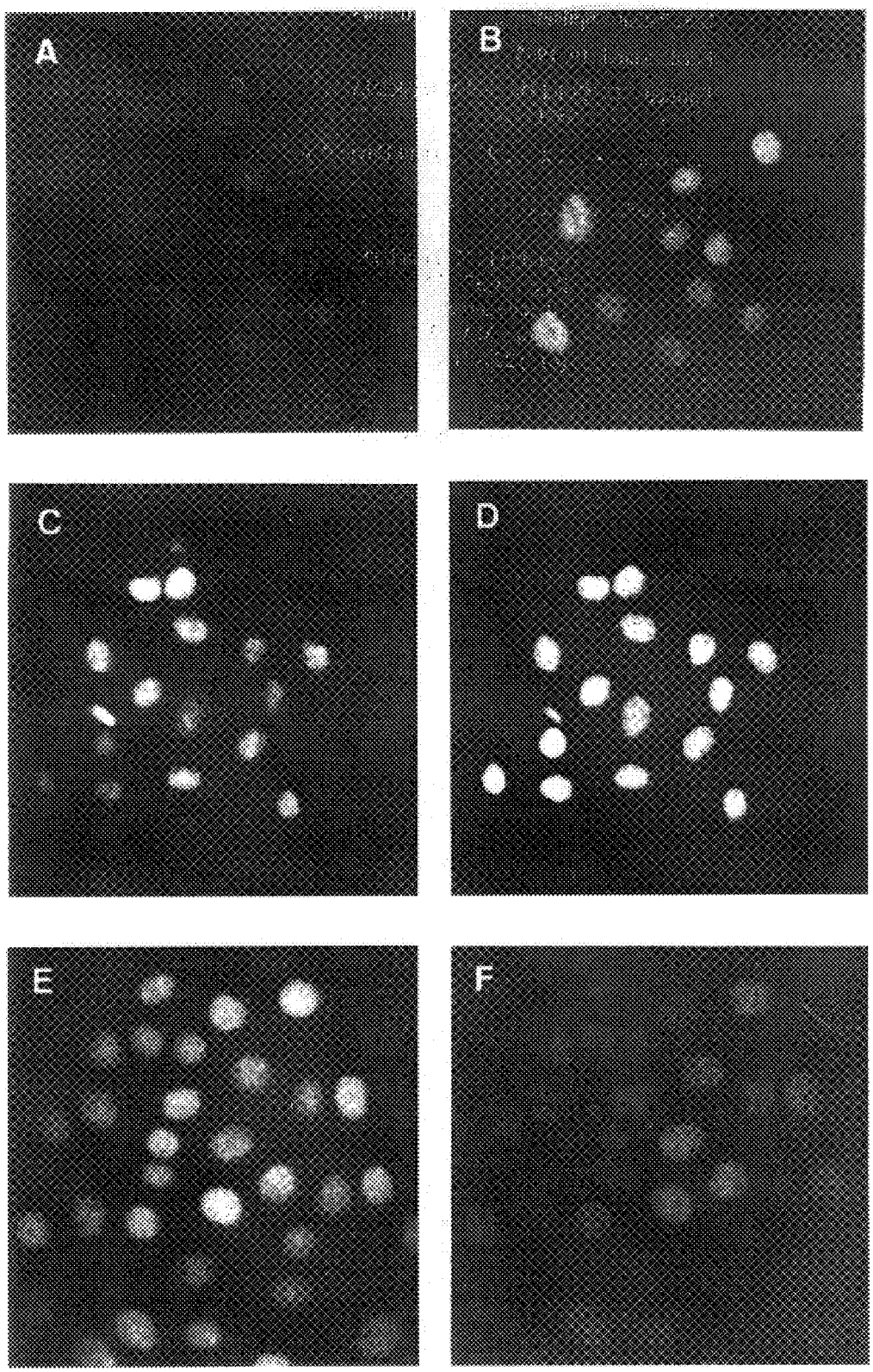
FIG. 4A shows the phosphorylation of pRb in vivo. Hyperphosphorylated pRb has a lower affinity for the nuclear compartment compared to the hypophosphorylated subtypes and can be extracted from the nucleus by using a hypotonic buffer containing Triton X-100(26). Panels A, C and E show staining with anti-pRb monoclonal antibody and B, D and F show the same field of cells stained with Hoescht. HaCaT cells were serum starved for 72 hours before serum addition. Peptide 6 coupled to Penetratin (panel C) or Penetratin by itself (panel A) was added at 8 hours after serum addition at 100 nM and the amount of phosphorylated pRb was estimated at 23 hours by determining pRb extractability (panels A and C) compared with a non-extracted staining (panel E).

When starved cells were incubated with the p16 peptide coupled to the carrier molecule or the carrier molecule alone at 10 hours post serum addition a difference in pRb extractability could be observed when assayed at 23 hours (26). Approximately 60% of the cells incubated with peptide 6 stained with an anti-pRb monoclonal antibody compared to only 14% incubated with the carrier only (FIG. 4A). This observation was confirmed by Western blot analysis of whole HaCaT cell extracts treated in a similar fashion (FIG. 4B). The results suggest that the number of cells carrying hypophosphorylated pRb increased significantly at 23 hours after serum stimulation when peptide 6 coupled to the carrier peptide was added before 12 hours. It also implies that the inhibition of cdk4-cyclin D activity observed in baculovirus infected Sf9 cell extracts (FIG. 2) is taking place in vivo.

The consistent inhibition of S-phase entry after adding the coupled peptides between 0 and 12 hours suggests that the effect of the peptide is persistent and that the carrier linked peptide is not rapidly degraded in the cells. This is consistent with reports suggesting that the Antennapedia homeodomain carrier peptide is protected from proteolytic degradation in the cell (24).

Refinement of the cdk Binding Motifs of p16 and Comparison with Other Proteins

The results above show that a 20aa peptide derived from the third ankyrin like repeat of p16 has similar features as the full length protein, e.g. binding to the cyclin-dependent dependent kinases cdk4 and cdk6 and to inhibit cdk4-cyclin D1 kinase activity in vitro as well as to block cell cycle progression. This region included the peptide sequence that corresponds to aa 84 to 103 of the full length p16 protein and is identical to the corresponding region of p15 and highly conserved in p18 and p19 as well as in the mouse p16.

Since members of the INK family of kinase inhibitors inhibit CDK-cyclin D kinase activity specifically by direct interaction with cdk4 and cdk6, we wanted to see whether this activity can be determined to one highly conserved domain shared between these proteins. Since it is mainly p16, and to a lesser extent p15, of the INK family that is associated with tumour suppressor activity it will be important to know if these different proteins inhibit the CDK-cyclin D kinase complex in a similar fashion through the same domain suggesting that the regulation of expression of these different proteins determines their role as tumour suppressors rather than their mean of action. Thus, we carried out experiments to see if this peptide domain could be further minimized and substituted with modified amino acid residues that are insensitive to proteane degradation in order to improve its potential as a model for a synthetic tumour suppressor peptide.

Figure 5A:
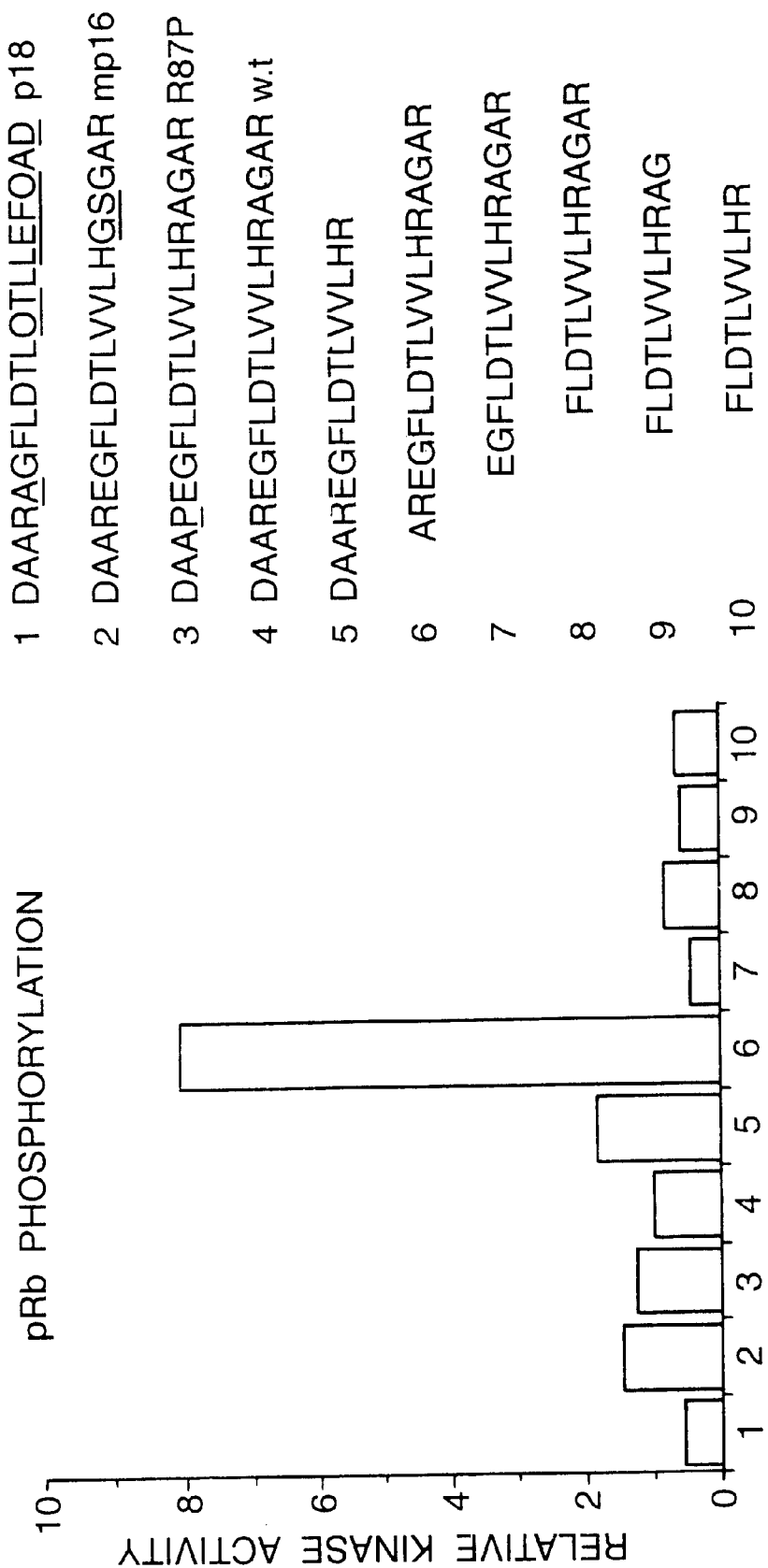
FIG. 5A shows the relative inhibition of pRb phsphorylation by p16, related peptides from corresponding regions of other INK family members and fragments of p16. In particular, it shows the effect of reducing the size of the p16 fragment on pRb phosphorylation.

To study the binding of peptides to cdk4 and cdk6 we expressed the proteins in a coupled in vitro reticulocyte translation system in the presence of $^{35}$S labelled methionine. A biotin group coupled to a Ser-Gly-Ser-Gly-linker at the N-terminus of the peptides was coupled to streptavidin coated agarose beads and incubated with the cell lysates. FIG. 5A shows the results measuring pRb phosphorylation, with FIGS. 5B and 5C showing the determination of the binding of the INK family members and the p16 peptide fragments to cdk4 and cdk6.

FIGS. 5A–C show that peptides, corresponding to the 84–103 region of p16, derived from p18 and mouse p16 inhibit pRb phosphorylation, as reflected in their capacity to inhibit pRb phosphorylation by Sf9 insect cell lysates over-expressing cdk4 and cyclin D1, and binds to both cdk4 and cdk6 in a similar way.

We then tested a p16 peptide deletion series which was made by deleting two residues at the same time from either the N- or C-terminus. We found that removing 2 residues at the N-terminus (peptide 6 in FIGS. 5A–C) severely reduced both the cdk binding and the kinase inhibitory effect and that the activity could be restored when another two residues were deleted at either terminus. Peptide 10 only includes the 10 residues that correspond to a motif that is conserved among ankyrin like repeats and is predicted to. form a tight secondary helical structure. This peptide has lost some of its binding capacity but is still a good kinase inhibitor demonstrating that the original 20 amino acid p16 peptide can be reduced with at least 10 residues and still inhibit CDK-cyclin D1 kinase activity. This deletion series and the alanine scan shows that in the peptides we examined there was a strong correlation between binding and kinase inhibition.

It is interesting to notice that the R87P substitution does not hamper the function of the peptide. Since this mutation, like most p16 mutations so far detected, is located outside the region that is shown to be important for the peptide interaction with the cdk, it suggests that these mutations will induce conformational changes of the protein that will effect the central ankyrin like domain. This hypothesis is strengthened by recent NMR studies showing that P114 and G101W give rise to global conformational changes of the protein and that the R87P mutation has been shown to be temperature sensitive.

Similar explanations might also give an answer to the surprising observations that the peptide loses its effect when two residues are taken off the N-terminus, suggesting that these deletions causes conformational changes of the peptide. The minimal binding peptide (peptide 10) basically consists of two hydrophobic regions surrounded by polar residues that could form an amphipatic helical wheel. The p18 peptide carries 8 substitutions, compared to the p16 peptide, and the QT at positions 95 and 96 would at first seem to disturb the binding domain of the peptide since these disrupts the second hydrophobic pocket. However, this peptide carries two hydrophobic residues at position 97 and 98 instead which are surrounded by polar residues and it also has the GFLD (SEQ ID NO:5) region intact, as well as leucine 98, which might suggest that the second hydrophobic pocket can be moved a few residues toward the C-terminus without effecting cdk binding.

Thus, these results show that after initial reductions in the size of the p16 fragments resulted some reduction in cdk inhibition (see peptide 6), further reduction in the size of the p16 fragments once again increased the inhibition (peptides 7 to 10). This demonstrates that small peptides comprising 16 aa (peptide 7), 14 aa (peptide 8), 12 aa (peptide 9) and 10 aa (peptide 10) are able to exert a biological effect which is the same or analogous to that of full length p16. These results also support the idea that two motifs of p16 are important for kinase binding, a FLD motif and a LVVL motif.

Accordingly, these results indicate that the 20 aa fragment of p16 disclosed above (residues 84 to 103) can be made at least 50% smaller and still be active.

Alanine Substitution at Positions 95 and 96

The results above from an alanine scan substitution series of the p16 peptide suggested that the two valines at position 95 and 96 could be important for the binding of the peptide to cdk and for its kinase inhibitory function, and that substitution of aspartic acid 92 to alanine would potentiation both binding and kinase inhibitory capacity. It is also clear from the peptide deletion series that these residues are within the 10 residues that mediate binding of the peptide.

Accordingly, to investigate this further, we introduced the VV95;96AA and the D92A mutations into the highly purified peptides that were linked to the third domain of the Antennapedia homeodomain for transporting peptides across biological membranes and the VV95;96AA into the full length protein in order to see if residues that seem important for peptide binding to cdk4 and cdk6 also influenced the binding off the full length protein. The VV95;96AA mutations were introduced into a His-tagged wild type p16 and expressed in E. coli and the corresponding peptides were synthesized at 99.9% purity.

Figure 6A:
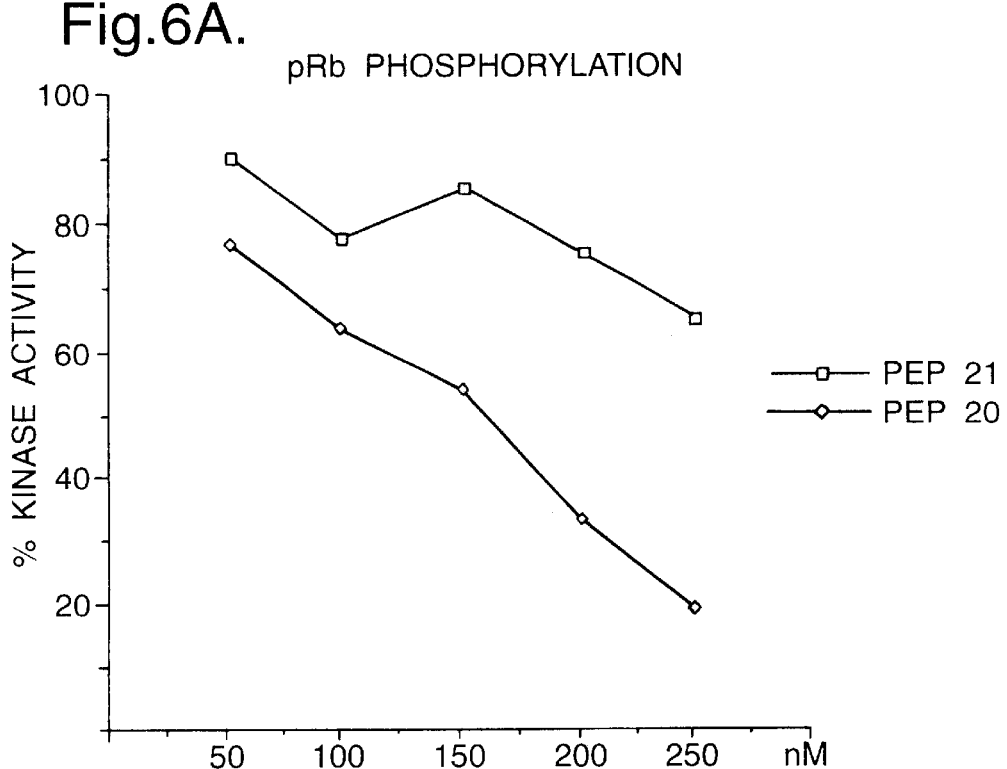
FIGS. 6A and 6B show the graphs indicating the effect of increasing concentrations of peptides 20 and 21 (FIG. 6A) and wt p16 and V95,96A p16 (FIG. 6B) on the inhibition of cdk-cyclin D kinase activity. Peptide 20 is a 36aa long synthetic peptide that carries the D92A mutation and peptide 21 carries the VV.95,96AA mutation.
Figure 6B:
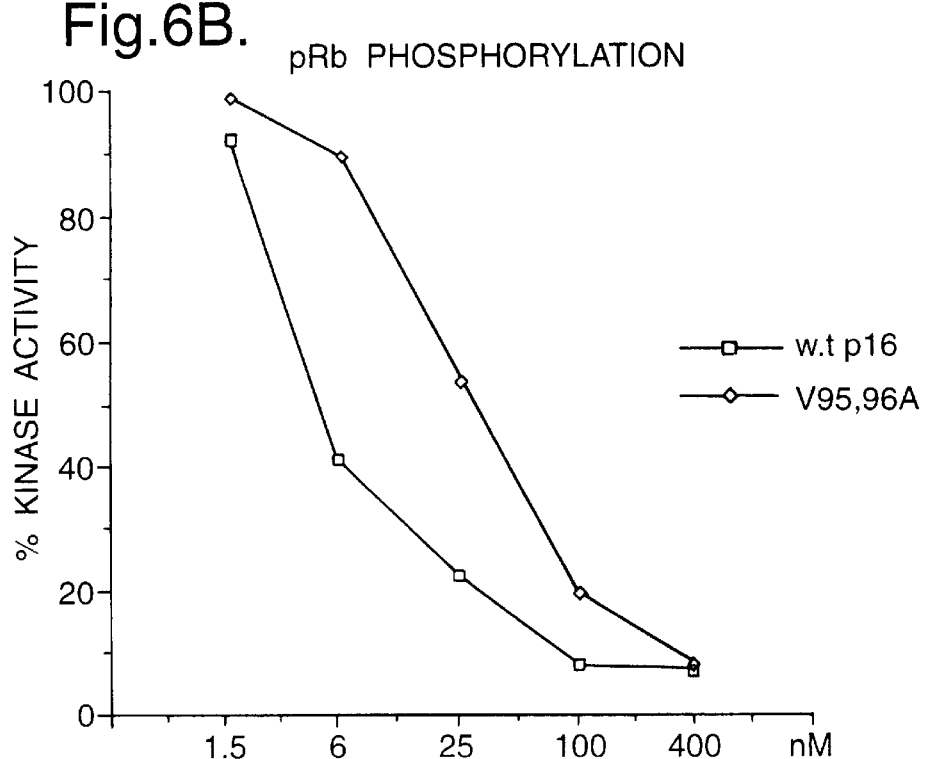

FIGS. 6A and 6B show the results of these studies. The results show that peptide 21, which has the two VV95,96AA substitutions, is significantly less active in vivo. The same peptide is also less active in inhibiting the cdk-cyclin D kinase activity in vitro. This confirms the results of the first alanine scan described above which suggested that these residues are important for the peptide to bind to cdk4 and cdk6.

When the same substitutions are put into the wild type His-tagged p16 protein a similar loss of kinase inhibitory activity is observed (in both cases the 50% kinase inhibitory concentration is increased about 5-fold). While we do not wish to be bound by any particular theory, these results further support the view that these residues are involved in direct binding of the peptide fragments of p16, as well as the full length protein, to cdk4 and cdk6, i.e. the mechanism of kinase inhibition is the same in the full length p16 and the peptide fragments described here.

In vivo, at the same concentration, the peptide 20 induces an almost complete block of S-phase entry in HaCaT cells, whereas the pep21 has only marginal effect at a 10 $\mu$M peptide concentration.

Response to p16 in Different Cell Lines

Mouse embryonic fibroblast (MEF) from mice that are p16(-/-) (knockouts) and from normal p16(+/+) were tested for response to the p16 peptides linked to Penetratin described above. After 12 hours of treatment with the same amount of the p16 peptide linked to Penetratin there is an increase of 42% of the (-/-) cells population in G1 compared to 9% of the (+/+). After 24 hours the figure is 22% compared to 5%. At the same time the decrease in S phase is 33% for the (+/+) 30%. Taken together, these results suggest that p16(-/-) MEFs are more sensitive to the p16 peptide than the (+/+).

We have also tested some other cell lines and we see effect in cells derived from fibroblast, epithelial and muscle origin, and these show a similar suppression of growth in response to p16 peptide. By way of comparison, no growth suppression was observed in a Saos 2 (pRb negative cell line), confirming the biological action of p16 is through the inhibition of pRb phosphorylation. These results are summarised in Table 1.

We have also carried out experiments to see whether p16 peptide will inhibit the differentiation of mouse myoblast cells (C2C12 cells) into myotube cells. These results show that when C2C12 cells are put in 0.5% FCS medium they will stop growing and from multinucleated myotubes. However, if they are treated with the p16 peptide they will, in addition to stopping growing, also inhibit the formation of multinucleated myotubes in the presence of 0.5% FCS.

TABLE 1

| Tested cell lines | Growth suppressor effect by p16 peptide | Source |
|---|---|---|
| p16(-/-) | ++ | |
| C2C12 | ++ | |
| HaCaT | +++ | human keratinocyte line |
| human primary keratinocytes | +++ | |
| MRC5 | + | human fibroblast |
| MCF7 | +++ | human breast cancer derived line |
| MEF+/+ | + | mouse embryo fibroblast p16 positive |
| 3T3 | ++ | mouse fibroblast line |
| Saos 2 | - | pRb negative tumour cell line |

We have also observed that epithelial cells treated with the p16 peptide will alter the morphology of the cell-colonies to a more dense and rounded up phenotype. This is associated with an increase in the cells adhesion to tissue culture dish resulting in 6×increase in time before the cells will come off after trypsin treatment, demonstrating that the peptides will change cell adhesion properties. The modification of cellular adhesion properties has applications in preventing the spread of a tumour to form secondary tumours, providing a method for modulating the invasive capacity of tumour cells.

Finally, preliminary results suggest that the peptide are associated with senescence in human keratinocyte derived cells (HaCaT cells) as determined by a Beta-Gal assays. This is also important since it has been suggested that one of the physiological functions of the p16 protein involves senescence mechanisms which might be linked to its tumour suppressor role in vivo. The assay for identifying senescence in cells is described in Dimri et al, P.N.A.S., 1995, page 9396 seq.

FACS Analysis

Figure 7:
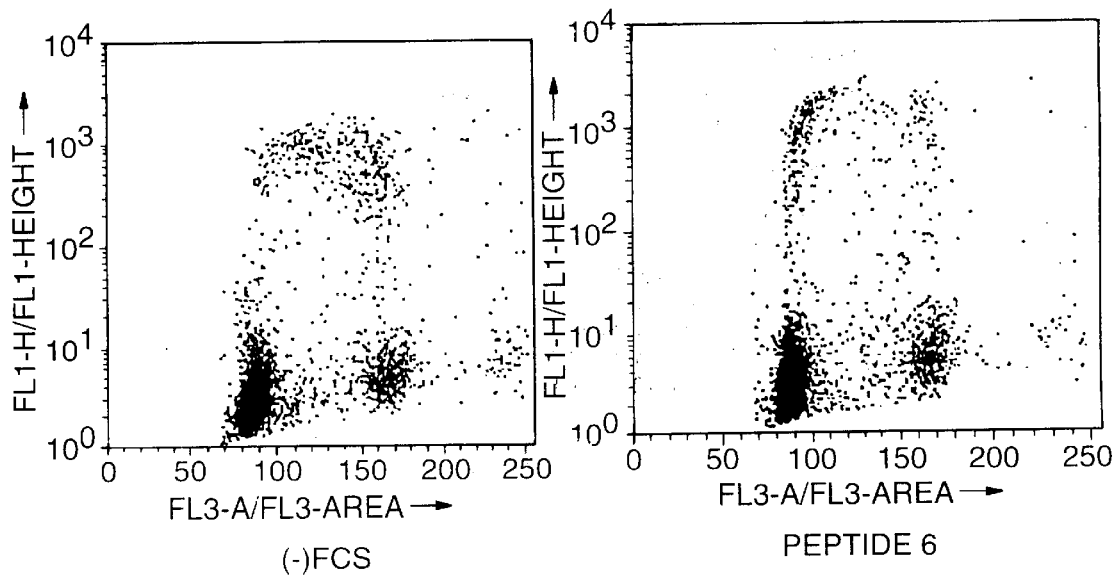
FIG. 7 shows the results from FACS analysis of HaCaT cells treated with three different peptides 36aa peptide consisting of a 16aa Penetratin sequence coupled to a 20aa peptide (peptide 6, the V95,96A and the D92A mutant p16 peptide) so that the Penetratin sequence is at the N-terminus of the 20aa peptides (i.e. N-Penetratin-p16-C). In these experiments, the cells were starved for 72 hours before 10% PCS and the peptides were added and analysed 2 hours later.
Figure 7:
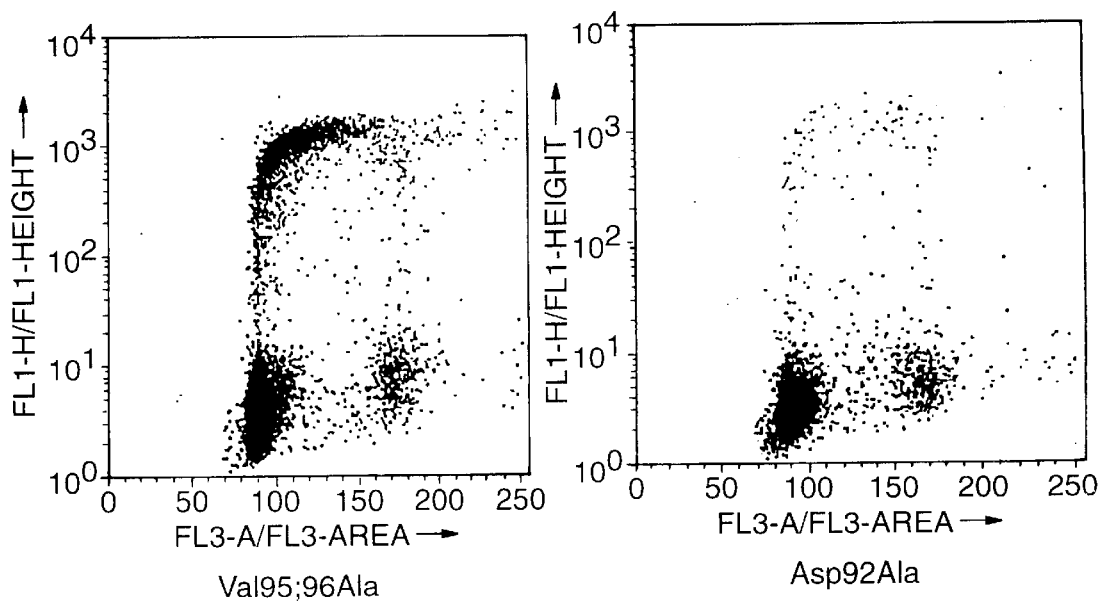

FIG. 7 shows the results from FACS analysis of HaCaT cells treated with three different peptides 36 aa peptide consisting of a 16aa Penetratin sequence coupled to a 20aa peptide (peptide 6, the V95,96A and the D92A mutant p16 peptide). These graphs show that the cells that do not get FCS are in the G1 phase and have been arrested properly by the addition of the peptides.

Conclusions

These results demonstrate that a 20 aa synthetic peptide corresponding to residues 84 to 103 of the p16 protein can mimic essential biochemical and biological properties described for the full length wild type p16 protein. Most important is the discovery that the peptide coupled to a small carrier molecule has the capacity to inhibit cell proliferation in vivo after direct addition to the tissue culture medium. This method generically broadens the application of small peptides in studying biological events in vivo and, in this case, may allow them to be used to replace specific suppressor gene function for therapeutic applications and to serve as models for identifying targets for novel antiproliferative drugs.

As a number of different tumours show defects in the pRb phosphorylation regulatory pathway, including over expression of cdk4 and cyclin D1, as well as showing loss of p16 function. All these tumours are potential candidates for a drug that would inhibit cdk-cyclin D activity in vivo.

REFERENCES

The references mentioned in this application are all herein incorporated by reference.
1. Serrano, M. et al. Nature, 366, 704–707 (1993)
2. Serrano, M. et al. Science, 267, 249–252 (1995)
3. Lukas, J. et al. Nature, 375, 503–506 (1995)
4. Koh, J. et al. Nature, 375, 506–510 (1995)
5. Parry, D. et al. EMBO J., 14, 503–511 (1995)
6. Weinberg, R., Cell 81,323–330 (1995)
7. Sherr, C. & Roberts, J., Genes & Development 9, 1149–1163 (1995)
8. Hunter, T. & Pines, J., Cell 79, 573–582 (1994)
9. Kamb, A. et al., Nature Genetics 8, 22–26 (1994)
10. Caldas, C. et al., Nature Genetics 8, 27–31 (1994)
11. Schmidt, a. et al., Cancer Research 54, 6321–6324 (1994)
12. Ranade, K. et al., Nature genetics 10, 114–116 (1995)
13. Okamoto, A. et al., P.N.A.S. 91, 11045–11049 (1994)
14. Mori, T. et al., Canc. Res. 54, 3396–3397 (1994)
15. Spruck, C. et al., Nature 370, 183–184 (1994)
16. Warbrick, E. et al., Current Biology 5, 275–282 (1995)
17. Picksley, S. M. et al., Oncogene 9, 2523–2529

18. Moodie, S. A & Wolfman, A., Trends Genet. 10, 44–18 (1994)
19. Pawson, T. & Schlessinger, J., Current Biology 3, 434–442 (1993)
20. Hannon, G. J. & Beach, D., Nature 371, 257–261 (1994)
21. Guan, K-L, et al., Gene & Dev. 8, 2939–2952 (1994)
22. Hirai, H. et al., Mol. & Cell. Biol. 15, 2672–2681 (1995)
23. Chan, F. et al., Mol. & Cel. Biol. 15, 2682–2688 (1995)
24. Derossi, D. et al., J. Biol. Chem. 269, 10444–10450 (1994)
25. Geng, Y. & Weinberg, R., P.N.A.S. 90, 10315–10319 (1993)
26. Mittnacht, S. & Weinberg, R., Cell 65, 381–393 (1991).

What is claimed is:

1. A peptide 20 amino acids or less in length that has the property of binding to cyclin dependent kinase (cdk) 4 or cdk6, wherein the peptide is:
  (a) a peptide consisting of the amino acid sequence DAAREGFLDTLVVLHRAGAR (SEQ ID NO: 1), or
  (b) an active portion of the peptide of (a), which retains the property of binding to cdk4 or cdk6, or
  (c) a derivative of the peptide of (a), which retains the property of binding to cdk4 and/or cdk6, and which has an amino acid sequence that includes insertion, addition, deletion or substitution of one or more amino acids relative to the amino acid sequence of (a), but that retains the amino acid motifs FLD and/or LVVL.

2. The peptide of claim 1, which is an active portion of the peptide of (a), and which includes the amino acid motifs FLD and/or LVVL (SEQ ID NO: 2).

3. The peptide of claim 2, which is an active portion or derivative of the peptide of (a), and which includes the amino acid motifs FLD and LVVL (SEQ ID NO: 2), separated by one or more amino acid residues.

4. The peptide of claim 1, which is a derivative of the peptide of (a), in which the aspartic acid residue of the amino acid motif FLD is replaced by a hydrophobic amino acid residue.

5. The peptide of claim 4 wherein the hydrophobic amino acid residue is alanine.

6. The peptide of claim 1 wherein the peptide is linked to a coupling partner selected from the list consisting of: a peptide consisting of the amino acid sequence RQIKIW-FQNRRMKWKK (SEQ ID NO: 3); and biotin.

7. A peptide of claim 1 that is an active portion of the peptide of (a), and that has an amino acid sequence chosen from the group consisting of:
  (a) DAAREGFLDTLVVLHR (SEQ ID NO: 11);
  (b) EGFLDTLVVLHRAGAR (SEQ ID NO: 13);
  (c) FLDTLVVLHRAGAR (SEQ ID NO: 14);
  (d) FLDTLVVLHRAG (SEQ ID NO: 15); and
  (e) FLDTLVVLHR (SEQ ID NO: 16).

8. The peptide of any one of claims 1–7, wherein the peptide is in the L isoform.

9. The peptide of any one of claims 1–7, wherein the peptide is in the D isoform.

10. An isolated nucleic acid molecule encoding the peptide of any one of claims 1–7.

11. A vector incorporating the nucleic acid molecule of claim 10 operably linked to expression control sequences.

12. A pharmaceutical composition comprising one or more peptides of any one of claims 1–7, in combination with a physiologically acceptable carrier.

13. A method of using the pharmaceutical composition of claim 12 for the treatment of a hyperproliferative disorder comprising administering the pharmaceutical composition to a subject in an amount sufficient to treat the disorder.

14. The method of claim 13 wherein the hyperproliferative disorder is cancer, psoriasis or arteriogenesis.

15. The method of claim 13, wherein the hyperproliferative disorder is associated with the overexpression of cdk4 or cdk6.

16. The method of claim 13, wherein the hyperproliferative disorder is cancer which is p 16 negative.

17. A method of identifying compounds which bind to the peptide of claim 1, the method comprising:
  (a) exposing the peptide to a candidate compound; and,
  (b) detecting the binding of the candidate compound to the peptide.

18. A method of identifying compounds which compete with a peptide of claim 1 for binding to cyclin dependent kinase (cdk) 4 or cdk6, the method comprising:
  (a) binding a detectably labeled predetermined quantity of the peptide to cdk4 or cdk6;
  (b) adding a candidate compound; and,
  (c) determining the amount of the labeled peptide that remains bound to the cdk4 or cdk6 or which becomes displaced by the candidate compound.

19. The method of claim 18 wherein the cdk4 or cdk6 are produced in reticulocyte lysates.

20. The method of claim 18, wherein the candidate compounds are selected from a synthetic combinatorial library.

21. The method of claim 17 or 18, further comprising determining the level of pRb phosphorylation in the presence and absence of the candidate compound, wherein a reduction in the level of pRb phosphorylation in the presence of the candidate compound is indicative that the candidate compound inhibits pRb phosphorylation.

22. The method of claim 17 or 18, further comprising determining the percentage of cells synchronized in $G_0$ which enter S-phase upon serum stimulation in the presence or absence of the candidate compound, wherein a reduction of the percentage of cells entering S-phase in the presence of the candidate compound is indicative that the candidate compound inhibits entry of cells into the S-phase.

* * * * *